(12) United States Patent
Lopez et al.

(10) Patent No.: US 8,889,630 B2
(45) Date of Patent: Nov. 18, 2014

(54) METHOD FOR HAIR REGROWTH USING GRANULOCYTE-COLONY STIMULATING FACTOR

(71) Applicants: Carlos Lopez, Carmel, IN (US); James K Petell, Wakefield, RI (US)

(72) Inventors: Carlos Lopez, Carmel, IN (US); James K Petell, Wakefield, RI (US)

(*) Notice: Subject to any disclaimer, the term of this patent is extended or adjusted under 35 U.S.C. 154(b) by 0 days.

(21) Appl. No.: 13/721,111

(22) Filed: Dec. 20, 2012

(65) Prior Publication Data

US 2013/0164252 A1 Jun. 27, 2013

Related U.S. Application Data

(60) Provisional application No. 61/579,975, filed on Dec. 23, 2011.

(51) Int. Cl.
| | | |
|---|---|---|
| A61P 17/14 | (2006.01) |
| A61K 45/00 | (2006.01) |
| A61K 35/14 | (2006.01) |
| A61K 38/19 | (2006.01) |
| A61Q 7/00 | (2006.01) |
| A61K 8/98 | (2006.01) |
| A61K 35/12 | (2006.01) |
| A61K 8/64 | (2006.01) |

(52) U.S. Cl.
CPC ............... *A61K 38/193* (2013.01); *A61K 35/14* (2013.01); *A61Q 7/00* (2013.01); *A61K 8/983* (2013.01); *A61K 35/12* (2013.01); *A61K 8/64* (2013.01)
USPC ......................................... 514/20.7; 424/85.1

(58) Field of Classification Search
CPC combination set(s) only.
See application file for complete search history.

(56) References Cited

U.S. PATENT DOCUMENTS

| | | | |
|---|---|---|---|
| 4,810,321 A | 3/1989 | Wank et al. | |
| 4,810,643 A | 3/1989 | Souza | |
| 5,214,132 A | 5/1993 | Kuga et al. | |
| 5,218,092 A | 6/1993 | Sasaki et al. | |
| 5,597,562 A | 1/1997 | Nomura et al. | |
| 5,599,690 A | 2/1997 | Fenton et al. | |
| 5,641,663 A | 6/1997 | Garvin et al. | |
| 5,676,941 A | 10/1997 | Souza | |
| 5,795,968 A | 8/1998 | Kuga et al. | |
| 5,994,518 A | 11/1999 | Kuga et al. | |
| 6,004,548 A | 12/1999 | Souza | |
| 6,027,720 A | 2/2000 | Kuga et al. | |
| 6,165,785 A | 12/2000 | Ogle et al. | |
| 6,261,250 B1 | 7/2001 | Phillips | |
| 6,261,550 B1 | 7/2001 | Osslund | |
| 6,379,661 B1 | 4/2002 | Souza | |
| 6,495,129 B1* | 12/2002 | Li et al. .................. | 424/85.1 |
| 6,497,689 B1 | 12/2002 | Schmidt et al. | |
| 6,830,705 B1 | 12/2004 | Freeland et al. | |
| 7,118,748 B1* | 10/2006 | Rodgers et al. ........... | 424/185.1 |
| 8,383,099 B2* | 2/2013 | Dudley et al. ............ | 424/93.7 |
| 2004/0141946 A1 | 7/2004 | Schaebitz et al. | |
| 2007/0116691 A1 | 5/2007 | Cambier et al. | |
| 2007/0212335 A1 | 9/2007 | Hantash et al. | |
| 2012/0238941 A1 | 9/2012 | Hantash et al. | |

FOREIGN PATENT DOCUMENTS

| | | | |
|---|---|---|---|
| WO | 0044785 A1 | 8/2000 | |
| WO | 2009062313 A1 | 5/2009 | |
| WO | WO2009/062313 * | 5/2009 | ............ A61K 38/19 |

* cited by examiner

*Primary Examiner* — Elly-Gerald Stoica

(74) *Attorney, Agent, or Firm* — James Petell

(57) ABSTRACT

The present invention provides a method for re-growing hair in patients with androgenic alopecia by administering effective consecutive courses of Granulocyte-Colony Stimulating Factor or derivatives. After the state of re-growth is obtained, the hair growth is maintained by administering periodic courses of Granulocyte-Colony Stimulating Factor or derivatives. The invention further provides a method for increasing cuticle growth and density using a similar administration of effective consecutive courses of Granulocyte-Colony Stimulating Factor or derivatives. The increased cuticle growth and density is maintained by administering periodic courses of Granulocyte-Colony Stimulating Factor or derivatives.

9 Claims, 4 Drawing Sheets

GCSF Treated Twin        GCSF Untreated Twin

METHOD FOR HAIR REGROWTH USING GRANULOCYTE-COLONY STIMULATING FACTOR

FIELD OF INVENTION

A method for reversing hair loss and the loss of cuticle growth and density by administering effective courses of Granulocyte-Colony Stimulating Factor.

BACKGROUND OF THE INVENTION

Parkinson's disease is an example of a progressive neurodegenerative disease. It is usually diagnosed in adulthood, usually when the patient is about 55 years of age, and is characterized by tremors, rigidity, and bradykinesia. It is well understood that many of the abnormalities found in these patients are due to the loss of dopamine (DA) neurons in the substantia nigra and the depletion of striatal dopamine levels. More recently, there has been a re-evaluation of the signs and symptoms found in Parkinson's disease patients that has led to the conclusion that Parkinson's disease is a systemic disease with involvement of peripheral nervous tissue. For example, the loss of the sense of smell has been found to be an early sign of Parkinson's disease reported in most patients. Often, the earliest sign of Parkinson's disease in patients is the loss of the sense of smell so that this symptom can be used as a diagnostic in patients with early disease. This symptom of disease is probably due to loss of neurons in the olfactory bulb of the brain. Also, orthostatic hypotension has been shown to be one of the more common signs of Parkinson's disease, probably due to a direct effect on the peripheral nervous system (PNS) of the host. Clinical manifestations of Parkinson's disease are not apparent until over 80% of the central or peripheral neurons have degenerated. Most new Parkinson's disease patients are started on dopamine (DA) agonists when first diagnosed, but usually progress to L-DOPA (L-dopamine), the precursor of dopamine in tissue. As a therapeutic, L-DOPA is used to relieve Parkinsonian motor signs, but has very little effect on PNS signs and symptoms of disease. In fact, its long-term use is usually associated with diminished efficacy and increasingly bothersome side effects. Other examples of chronic degenerative neurological disorders that might be treated in a similar manner include macular degeneration, urinary incontinence, Alzheimer's disease, Multiple Sclerosis, and short term memory deficiency. These disorders have in common three characteristics; they are usually diagnosed late in life, there is evidence of familial, but not Mendelian genetic inheritance of each disease, and patients will have had a period of time as adults before diagnosis of disease when the host appears to function normally without evidence of signs or symptoms of the chronic disease.

Over the past few years, tremendous strides have been made in understanding the crucial role that stem cells play in embryogenesis and organogenesis. Much of the accumulated data indicates that stem cells play an important role in the development and maturation of mammals. It is well known that each organ of the adult body contains progenitor stem cells that can respond to signals from other cells or injured tissue and migrate to the site of injury to help restore the tissue to normal health. In animal models, the "self-repair" system clearly responds to acute injury of tissues in the body and recruits stem cells from the bone marrow and other parts of the body to help with the repairs. Stem cells are also required to sustain those functional cell populations that turn over rapidly in the body such as skin and the various lymphocyte populations. The "self-repair" system is only now being demonstrated in human studies.

With the beginning of an understanding of the "self-repair" system and its probable role in response to tissue injury, researchers have proposed that delivering somatic progenitor stem cells directly to the site of damage might augment the hosts own "self-repair" system and more quickly and completely repair the damage to the host tissue. For example, neural stem cell lines have been successfully used to treat spinal cord injuries mice and rats. However, this "self-repair" response appears to be determined by a complex interaction between cells and protein mediators produced by host and donor cells. Understanding the factors involved and their roles in this response and the differentiated state of the cells involved will be crucial to devising methods for controlling and utilizing this system for providing new therapies for chronic diseases. Studies are ongoing in many laboratories to further define the factors and cells involved. Most recently, continuous infusion of Glial-Derived Neurotrophic Factor (GDNF), a stem cell growth factor, directly into the brain has been claimed to have benefit for patients with Parkinson's disease.

Over the past several years, significant interest has developed in using mobilized peripheral blood progenitor cells for allogeneic hematopoietic reconstitution. Treatment of stein cell donors with a five-day course of Granulocyte-Colony Stimulating Factor or its pegalated derivative, causes the release of stem cells from the bone marrow into the circulating blood and greatly increases the number of hematopoietic and other stem cells that could be harvested from the donor. This procedure requires Granulocyte-Colony Stimulating Factor be administered to otherwise normal donors in order to release stem cells into the peripheral blood where they can be collected by leukophoresis and prepared for transplantation. Many studies have reported the use of Granulocyte-Colony Stimulating Factor in normal volunteers and normal donors, usually at a dose of 5 to 10 micrograms per kg per day for 4 to 8 days. The most common side effect was bone pain. While the toxicities were frequent, the severity was generally mild and very few normal donors had to discontinue Granulocyte-Colony Stimulating Factor because of the side effects. Persons treated with Granulocyte-Colony Stimulating Factor were found to have a surge in peripheral blood stem cells 4 to 7 days after initial treatment. The use of Granulocyte-Colony Stimulating Factor for mobilizing peripheral blood stem cells is widespread and appears to be safe and to be capable of generating the stem cells needed for allogenic or autologous transplantation.

Although the above studies suggest Granulocyte-Colony Stimulating Factor is capable of mobilizing peripheral hematopoietic stem cells, it is not known if Granulocyte-Colony Stimulating Factor could induce the recruitment of either local or migration of peripheral stem cells to injured neural tissue, differentiate and restore neural function required for the slowly developing lesions found in most chronic diseases. Further, to our knowledge a "self-repair" system has not been described in human studies.

Diabetes is a major public health problem in the United States affecting 16 million people and accounts for one sixth of all health related expenditures. There are two types; Type 1 (insulin dependent diabetes) and Type 2 (noninsulin-dependent diabetes). Type 1 is characterized by beta cell loss and absolute insulin deficiency. Of the patients with diabetes today, approximately 90 to 95% of the inflicted are Type 2 diabetics. It is generally characterized by elevated fasting blood glucose and lack of sensitivity to insulin and impaired insulin secretion. The prevalence of Type 2 diabetes is about 7 percent for persons between 45 to 64 years of age. The microvascular and macrovascular complications of Type 2 diabetes causes significant morbidity and mortality in affected individuals. Diabetic retinopathy, neuropathy, and nephropathy are major causes of functional limitations and disability in this patient population. In the event that diet and exercise are not sufficient to control blood glucose, diabetics may be treated with one, and typically two, of several oral drugs able to lower blood glucose levels which include sulfonylureas, metformin, alpha-glucosidase, troglitazone, and repaglinide. These agents act on one of four mechanisms that alter renal function, liver metabolism, insulin secretion or breakdown of complex carbohydrates. If these drugs are insufficient, insulin treatment may be prescribed alone or together with these oral agents.

Improved glycemic control reduces the risk of microvascular complications in Type 2 diabetes. Despite this evidence, patients with Type 2 diabetes frequently do not maintain adequate glycemic control. However, the health outcomes of patients with Type 2 diabetes who are treated with insulin to control glycemia do much better than those that do not. Patients are encouraged to use intensive insulin treatment protocols to better control blood sugar but analysis of their outcomes indicate that it did not affect the quality of life of patients in the intensive insulin treatment nor did it have a significant protective effect against cardiovascular diseases. There is evidence that tight glycemic control will decrease the incidence of microvascular complications so patients should be encouraged to use insulin and oral hypoglycemic agents. However, it is difficult to make a convincing argument to patients that do not currently have severe symptoms of disease associated with their elevated blood sugar levels. There are no other forms of medical treatment to lower blood glucose to an acceptable range. The ideal drug for these patients is one where a single drug can be taken periodically that is able to control blood glucose levels over the course of a month or longer with reduced side affects.

It is unknown whether the chronic progressive neurodegenerative and non-neurodegenerative disorders could be treated effectively by mobilizing the "self-repair" mechanism of the host or even if that "self-repair" mechanism could be detected in patients with these disorders. Furthermore, Parkinson's disease in humans is a systemic disease with symptoms that indicate the PNS is an important target tissue of this disease. Surprisingly, this invention directly demonstrated for the first time in humans the potential action of Granulocyte-Colony Stimulating Factors, known to mobilize stem cells into the peripheral blood as well as to cause them to differentiate, to also be a therapy to reverse symptoms of an adult onset neurodegenerative disorder such as Parkinson's disease. In addition, it was even more surprising that Type 2 diabetes was found to be effectively controlled by periodically administering of Granulocyte-Colony Stimulating Factors offering a new approach and a revolutionary treatment for this disease. In both cases of adult onset disease, the patient receiving the drug was provided a long term reversal of all disease symptoms and this allowed him to live a more normal lifestyle. Also, the extended period of time between courses of GCSF might also result in a lower incidence of side effects from drug therapy.

SUMMARY OF THE INVENTION

The present invention is directed to provide a method of treating symptoms associated with a neurodegenerative disease in a human by administering an effective dose of Granulocyte-Colony Stimulating Factor or its derivatives or combinations thereof. More preferably, the invention is directed to provide a method for the reversal of symptoms associated with Parkinson's Disease in a human through periodically administering Granulocyte-Colony Stimulating Factor, or its derivatives, or combinations thereof.

In another aspect, the invention herein is directed to provide a method of treating symptoms associated with diabetes in humans by administering an effective dose of Granulocyte-Colony Stimulating Factor or its derivatives, or combinations thereof. More preferably, the invention is directed to provide a method for the extended reduction of blood glucose levels associated with Type 2 diabetes in a human through administering of Granulocyte-Colony Stimulating Factor, or its derivatives, or combinations thereof.

In the first aspect of the invention, one or more symptoms of an adult onset neurodegenerative disease are treated by administering to a human an effective dose of Granulocyte-Colony Stimulating Factor, or its derivatives, or combinations thereof. Adult onset neurodegenerative diseases include but are not limited to Parkinson's Disease, macular degeneration, urinary incontinence, age related short term memory loss, and multiple sclerosis. More preferably, one or more symptoms of adult onset Parkinson's disease are reversed by administering an effective dose of Granulocyte-Colony Stimulating Factor or its derivatives or combinations thereof.

In the second aspect of the invention, an effective dose of Granulocyte-Colony Stimulating Factor, or its derivatives, or combinations thereof is administered to a human with an adult onset neurodegenerative disease by subcutaneous injection, transdermal patch, intravenously, orally or other means. A typical period for administering Granulocyte-Colony Stimulating Factors is from about 1 to 8 days, preferably ranging 3 to 6 days.

In a third aspect of the invention an effective dose of Granulocyte-Colony Stimulating Factor, or its derivatives, or combinations thereof are administered daily to a human for treatment of an adult onset neurodegenerative disease ranging from 0.1 micrograms to 20000 micrograms per kg body weight per day, preferably between 1 to 20 micrograms per kg body weight per day.

In a fourth aspect of the invention an effective dose of Granulocyte-Colony Stimulating Factor or its derivatives, or its derivatives, or combinations thereof is administered to a human for treatment of an adult onset neurodegenerative disease for about 1 to 8 days and repeated about every 2 to 18 weeks, and more preferably every 4 to 10 weeks.

In a fifth aspect of the invention an effective dose of Granulocyte-Colony Stimulating Factor or its derivatives, or combinations thereof is administered into a human for the reversal of one or more symptoms associated with Parkinson's Disease. Symptoms of Parkinson's Disease may be either central nervous system or peripheral nervous system derived and, include but are not limited to, orthostatic hypotension, resting tremor, rigidity, postural instability, micrographia, urinary and gastrointestinal incontinence and lack of sense of smell.

In a sixth aspect of the invention an effective dose of Granulocyte-Colony Stimulating Factor or its derivatives, or combinations thereof is administered into a human with an adult onset neurodegenerative disease or condition in combination with stem cells, selected from a group consisting of harvested adult progenitor stem cells or stem cell lines. In a related aspect, harvested adult progenitor stem cells or stem cell lines are pre-treated with Granulocyte-Colony Stimulating Factor or its derivatives or combinations thereof before injection.

In a seventh aspect of the invention, the level of blood glucose in an adult onset Type 2 diabetic is reduced by treatment with an effective dose of Granulocyte-Colony Stimulating Factor or its derivatives, or its derivatives, or combinations thereof. Preferably the blood glucose levels after treatment remain reduced by 2 days longer, more preferably 1 week or longer and most preferably 4 weeks or longer.

In the eighth aspect of the invention, an effective dose of Granulocyte-Colony Stimulating Factor or its derivatives or combinations thereof is administered into a human for treatment of diabetes, and preferably Type 2 diabetes, by subcutaneous injection, transdermal patch, intravenously, orally or other means. A typical period for administering is from about 1 to 8 days, more preferably ranging 3 to 6 days.

In the ninth aspect of the invention an effective dose of Granulocyte-Colony Stimulating Factor, or its derivatives, or combinations thereof administered into a human for treatment of diabetes ranging from 0.1 micrograms to 20000 micrograms per kg body weight per day, preferably between 1 micrograms to 20 micrograms per kg body weight per day.

In the tenth aspect of the invention an effective dose of Granulocyte-Colony Stimulating Factor or its derivatives, or combinations thereof is administered for treatment of Type 2 diabetes for about 1 to 8 days and the treatment is repeated about every 2 to 18 weeks, and preferably every 4 to 10 weeks. Preferably, Granulocyte-Colony Stimulating Factors is administered at least one week before the blood glucose levels rise to the levels prior to treatment.

In an eleventh aspect of the invention, Granulocyte-Colony Stimulating Factor or its derivatives, or combinations thereof is effective in improving other brain associated neural diseases that include but are not limited age related memory impairment, Schizophrenia, and Alzheimer's.

In the twelfth aspect of the invention, an effective dose of Granulocyte-Colony Stimulating Factor, or its derivatives, or combinations thereof for accelerating hair re-growth or cuticle growth and density when administered for about 3 to 6 days and the treatment is repeated about every 3 to 8 days for two or more consecutive courses, preferably 3 to 6 courses. An effective dose of Granulocyte-Colony Stimulating Factor, or its derivatives, or combinations thereof are administered daily to a human for treatment for hair re-growth or cuticle growth ranging from 0.1 micrograms to 20000 micrograms per kg body weight per day, preferably between 0.1 to 10 micrograms per kg body weight per day.

In the thirteenth aspect of the invention, an effective dose of Granulocyte-Colony Stimulating Factor, or its derivatives, or combinations thereof for maintaining hair growth or cuticle growth and density when administered for about 3 to 6 days and the treatment is repeated about every 2 to 18 weeks, and preferably every 6 to 12 weeks. An effective dose of Granulocyte-Colony Stimulating Factor, or its derivatives, or combinations thereof are administered daily to a human for hair treatment from 0.1 micrograms to 20000 micrograms per kg body weight per day, preferably between 0.1 to 10 micrograms per kg body weight per day.

In the fourteenth aspect of the invention, an effective dose of Granulocyte-Colony Stimulating Factor or its derivatives, or combinations thereof is administered into a human to restore or maintain hair growth or cuticle growth in combination with adult stem cells, selected from a group consisting of or stem cell lines or harvested adult donor stem cells or progenitor stem cells from an individual administered with Granulocyte-Colony Stimulating Factor or its derivatives. Other compounds that increase the mobilization of stem cells when used with Granulocyte-Colony Stimulating Factor or its derivatives may optimize production of donor adult stem cells. Adult stem cells obtained from self from 16 to 35 years of age and more preferably from self from 20 to 25 years of age. In a related aspect, adult stem cells, progenitor stem cells or stem cell lines are pre-treated with Granulocyte-Colony Stimulating Factor or its derivatives or combinations thereof before injection.

"Granulocyte-Colony Stimulating Factors" means Granulocyte-Colony Stimulating Factor or its derivatives, or other biologically or chemically derived compounds or factors that are functional equivalent.

"Maintaining" means slowing, interrupting, arresting or stopping the progression of the disease or condition.

"Reversing" means the improvement of one or more symptoms from the diseased state or condition rather than maintaining the current state of disease.

"Re-growth" means the growth of new hair in the scalp and other areas due to conditions of hair loss, preferably adult onset androgenic alopecia, rather than increased hair growth.

"Treat" means maintaining the state of the disease or condition or the reversal of a disease symptom or condition.

DETAILED DESCRIPTION OF INVENTION

Figure 1:
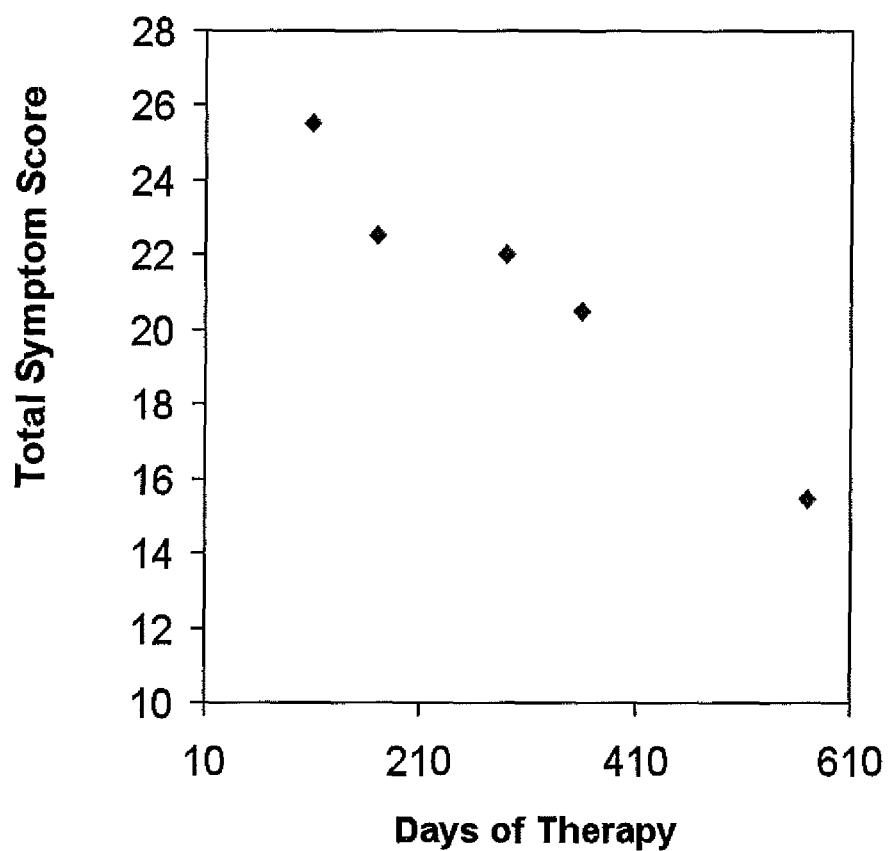
FIG. 1 demonstrates the long term reversal of Parkinson's Disease symptoms using the United Parkinson's Disease Scale to evaluate the condition of the patient administered with Granulocyte-Colony Stimulating Factor over two and one-half years.
Figure 2:
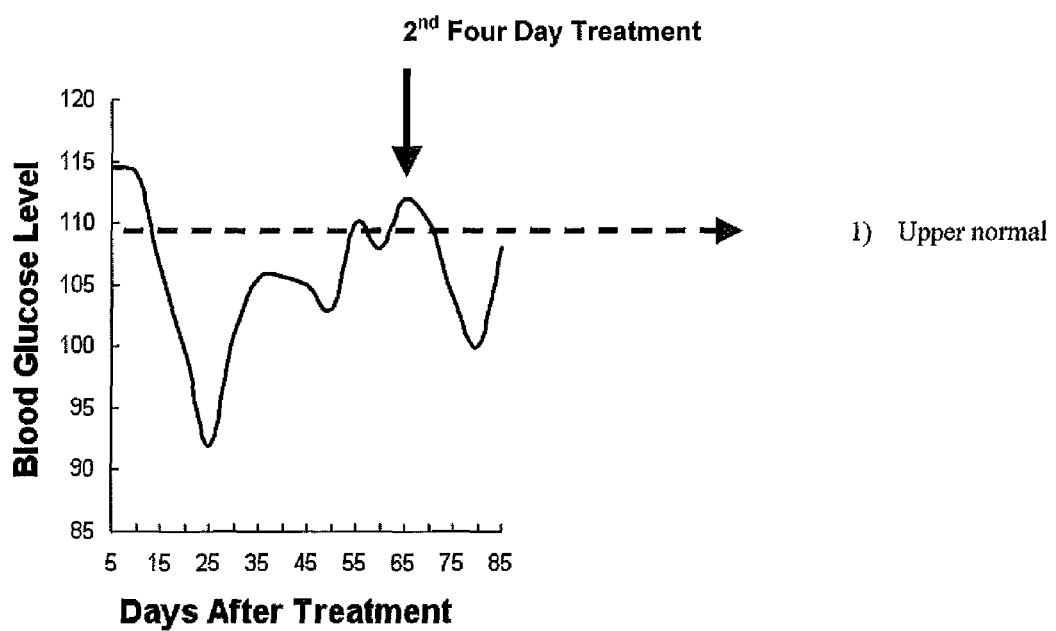
FIG. 2 demonstrates the reduction of blood glucose levels below the preferred normal limit after Granulocyte-Colony Stimulating Factor was administered to Type 2 diabetic patient.

The present invention described herein was aimed at performing treatments using Granulocyte-Colony Stimulating Factors administered to patients with neurodegenerative diseases, more preferably Parkinson's disease, to determine whether Granulocyte-Colony Stimulating Factors were able to maintain the state of the diseases, and preferably reverse the symptoms, either partially or completely. Unexpectedly, it was found that the treatment of the neurodegenerative disease, Parkinson's Disease, with Granulocyte-Colony Stimulating Factors reversed symptoms of both the central nervous system (CNS) and peripheral nervous system (PNS). In addition, it was found that Granulocyte-Colony Stimulating Factors delivered in an effective dose was able to reduce blood sugar levels of patients with adult onset Type 2 diabetes for a significant period of time.

The nucleic acid sequence and encoded amino acid sequence of Granulocyte-Colony Stimulating Factor (GCSF), also referred to as human pluripotent granulocyte colony-stimulating factor, as well as chemically synthesized polypeptides sharing its biochemical and immunological properties has been previously disclosed (U.S. Pat. Nos. 6,379,661; 6,004,548; 6,830,705; 5,676,941; 6,027,720; 5,994,518; 5,795,968; 5,214,132; 5,218,092; 6,261,550; 4,810,643; 4,810,321). Other examples of Granulocyte-Colony Stimulating Factor include analogs which retained their three-dimensional structures and hybrid molecules maintaining their biological and structural integrity were described by Osslund (U.S. Pat. No. 6,261,550). Examples of functional GCSF variants include any proteins, peptides or fragments thereof that are at least 70%, preferably 80% and most preferably at least 90% identity to full-length human GCSF amino acid sequence or its nucleotide sequence. Modifications of GCSF to improve functionality or resident serum clearance include but are not limited to polyethyleneglycol and polyethyleneglycol derivatives thereof, glycosylated forms (Lenogastrim™) (WO 00/44785), norleucine analogs (U.S. Pat. No. 5,599,690), addition of amino acids at either terminus to improve folding, stability or targeting, and fusion proteins, such as GCSF and albumin fusion protein (Albugranin™) (U.S. Pat No. 6,261,250). An increase in biological or functional activity over the native peptide may reduce the amount of dose and/or the time period required for treatment. Any chemical or biological entity that functions similar to GCSF can also be employed. GCSF, or the drug name Filgrastim, is currently being sold as Neupogen® and its polyethylene glycol modified or pegulated form, with the drug name Pegfilgrastim, sold as Neulasta™.

Examples of closely related functional forms include Granulocyte-Macrophage Colony Stimulating Factor (GMCSF) whose coding DNA sequence and protein including amino acid sequence are known as well as various methods employed to produce recombinant proteins (U.S. Pat. No. 5,641,663). Examples of functional GMCSF variants include any proteins, peptides or fragments thereof that are at least 70%, preferably 80% and most preferably at least 90% identity to full-length human GMCSF amino acid sequence or its nucleotide sequence. Modifications of GCSF to improve functionality or resident serum clearance include but are not limited to polyethyleneglycol and polyethyleneglycol derivatives thereof, glycosylated forms, norleucine analogs, addition of amino acids at either terminus to improve folding, stability or targeting, and fusion proteins, such as GCSF and albumin fusion protein (Albugranin™). An increase in biological or functional activity over the native peptide may reduce the amount of dose and/or the time period required for treatment. Any chemical or biological entity that functions similar to GMCSF can also be employed. Examples of GMCSF, or the drug name Sargramostim, which are currently being sold, include Leukine® or Leucomax® and Leucotropin®.

In one embodiment oral dosages, and methods thereof, of Granulocyte-Colony Stimulating Factor have been described by Nomura and Kazutoshi (U.S. Pat. No. 5,597,562) that allow for dosage reductions, facilitate dose control, and increase the practical usefulness of the bioactive proteins. In addition, Brimelow and Nanette (U.S. Pat. No. 6,497,689) have described preferred pH ranges comprising sulfate ions for stabilizations.

Granulocyte-Colony Stimulating Factors has been suggested to act as a neuroprotective agent in vitro and may be used for the potential treatment of diseases that result from oxidative stress or apoptosis such as in cerebral ischemia and traumatic brain injury (U.S. Pub. No. 2004/0141946). The work was focused on an in vitro model using STAT proteins and GCSF receptor or rat model for cerebral ischemia. It was suggested that GCSF may be used to "treat" broadly ischemic or hypoxic related diseases as well as neurological, psychiatric and neurodegenerative diseases as neuroprotective agent acting to slow, interrupt, arrest or stop the progression of the disease. However the work fails to provide insights on how treatment would work in humans as no human study was performed.

Type 2 diabetes is an example of a non-neurological disorder that appears to be due to the lack of insulin sensitivity of the target cells or insufficient levels of insulin in response to blood glucose. Although it is unknown what causes Type 2 diabetes, it is clear that the disease is usually first diagnosed as an adult and is usually progressive (in terms of the need for therapy to control blood sugar). Type 2 diabetics will have had a relatively long period of time with normal blood sugar before the fasting blood sugar levels begin to rise and the disease can be diagnosed. Other non-neurological disorders include osteoarthritis and benign prostate hypertrophy.

In view of ongoing research work on stem cells, the use of Granulocyte-Colony Stimulating Factors are likely to enhance or be required in the treatment of neurodegenerative diseases by stem cell therapy. For example, a method for the differentiation of stein cells in culture using Granulocyte-Colony Stimulating Factor and other factors, including lipopolysaccharides, to obtain immune system suppressor cells and immune systems stimulator cells was described by Ogle et al (U.S. Pat. No. 6,165,785). Using a similar approach, a method is useful in differentiating stem cells that are destined to become replacements for damaged cells in neurodegenerative disease and diabetes. Upon pretreatment of stem cells with Granulocyte-Colony Stimulating Factors, injected stimulated stem cells into patients with adult onset Type 2 diabetes and adult onset neurodegenerative diseases, such as Parkinson's Disease, are able to initiate repair or to enhance the effect over Granulocyte-Colony Stimulating Factors alone. The patient provided these stem cells is also administered Granulocyte-Colony Stimulating Factors for further benefit. Alternatively, patient with the adult onset diseases is injected with stem cells that are not pretreated with Granulocyte-Colony Stimulating Factors but subsequent treatment and provided with an effective dose of Granulocyte-Colony Stimulating Factors to enhance response.

In cases where the patient has a low or depleted level of stein cells due to age, being immunocompromised due to diseased, sickened state or like condition, the preferred treatment of patients requiring supplemental doses stem cells from those donors are those individuals that are histocompatibility similar or that match having nearly identical major histocompatibility complex (MHC) such an close relative or preferably a twin. A preferred source of stem cells is to administer a dose of the Granulocyte-Colony Stimulating Factors to the patient or close relative and collect the stem cells by methods well known in the art. The more preferred source of stem cells would be stem cells collected from the individual when the individual is between 16 to 35 years of age and most preferred when the individual is between 18 to 30 years of age. Once the stem cells are collected, the stem cells may be subjected to additional rounds of Granulocyte-Colony Stimulating Factors in vitro to increase the numbers of stem cells prior to treatment of the patient. In other embodiments, the multiplied stem cells are subjected to preservation methods, freezing at low temperatures and storage at less than −50° C. to ciyopreserve the cells until needed.

To optimize the production of stem cells in an individual, Granulocyte-Colony Stimulating Factors administered in conjunction with agonist and antagonist of ligand stromal derived factor-1 (SDF-1) to reduce expression of chemokine receptor CXDR4. Antagonist such as AMD3100 block the binding of SDF-1 and is known to cause rapid mobilization of CD34+ cells. With Granulocyte-Colony Stimulating Factors, AMD3100 (brand name Mozobil or Plerixafor) is effective in increasing the yield of CD334+ cells (J. Clin. Oncology, 2004, 1095-1102). Alternatively, an agonist peptide, CTCE-0021, may be more stable than natural SDF-1, which is rapidly cleaved by serum enzymes, has been reported to be an effective mobilizing agent. Other methods suggested to increase SDF-1 degradation are protease inhibitors such as MMP-9.

During the present invention, it was found that GCSF and likely related compounds are biological factors capable of mobilizing stem cells in the body and repairing or restoring specific functions of tissues. For any given cellular function, stem cells provide progenitor cells required by the body to restore specific functions of those tissues as evidenced by the effects on the more complex condition of Type 2 diabetes described herein. GCSF can cause the replication of those cells in response to specific mediators.

In another condition having a similar age related onset to Type 2 diabetes is age related androgenetic alopecia, referred to as male pattern baldness, which is the main cause of hair thinning or hair loss in adults. It is know that men with androgenic alopecia have lower levels of testosterone and increased amount of sex hormone-binding globulin that binds to testosterone. Interestingly, sex hormone-binding globulin is down regulated by insulin. Common but less than desirable treatments include minoxidil applied to the scalp to stimulate hair follicles and finasteride as an oral administration to slow hair loss but can have significant side effects. Finasteride acts to inhibit type II 5 alpha-reductase and subsequently inhibits conversion to DHT. Other routine treatments include hair transplants using plugs of hair from other areas of the scalp where hair continued to grow.

Recent investigations on improved treatments for hair loss have focused on those stem cells that are ultimately responsible for continued growth of hair. The growth of hair is not synchronized and grows in cycles in humans. It has three distinct phases of the hair growth cycle: anagen, catagen and telogen. The last phase, telogen, the keratinization is completed and the keratinized hair falls out. To replace the lost hair follicle, a new matrix is gradually formed from progenitor stem cells that are gathered in the basal layer in the outer root sheath bulge of the hair follicle. A new hair starts to grow from the matrix and the follicle returns to anagen, the hair growth phase.

Matrix cells derived from stem cells are under the influence of substances that control their growth and differentiation produced by cells of the dermal papilla. A large number of these factors are cytokines that influence or inhibit the proliferation of hair matrix cells and hair growth. Two factors believed to impact hair growth are keratinocyte growth factor (KGF) and insulin-like growth factor I (IGF-I) in animals.

Interestingly, nails are hardened epidermal variants of hair that grow continuously from the nail organ. The nail organ is an epidermal invagination on the dorsal side of the digit tips that is an equivalent of a large hair follicle. At the proximal end of the nail lies a matrix, a mass of stem cells that is equivalent to the pre-matrix cells in the hair follicle. The matrix is the immediate source of the cells that forms the nail. Unlike the loss of hair, typically nails become significantly weaker in aging as well as in response to fingernail cosmetics resulting in more brittle and flexible nails.

It has been unclear whether the loss of hair in humans, or androgenic alopecia, is caused by the inability of stem cells to mature into matrix cells that produce hair or due to a loss of stem cells or a subpopulation of stem cells that differentiate into matrix cell producing hair or a combination of both. However, a recent study suggested that balding might arise from stem cell activation rather a reduction in the number of stem cells in follicles present (J Clin Invest 2011, 121, 613). Further, they found that the same number of stem cells in the balding area, however the number of progenitor stem cells was markedly depleted in the scalp.

Other current approaches are exploring stem cell therapy for hair loss treatment. There has been considerable interest by numerous investigators in transplanting stem cells into hair follicles that are able to mature into functioning hair producing matrix cells. In one example, Hantash et al have taught of method of restoring hair by first irradiating the skin to create elongated voids in the skin. Once the voids created, stem cells such as hair follicle stem cells can be transplanted into the voids (U.S. Pat. App. Nos. 2007/0212335 and 2012/0238941). They teach that stem cells can be harvested from a variety of sources including adult hair follicles. In other related works, Cambier al taught a method to immortalize adult stem cells obtained from harvesting stem cell types of interest from the tissue or organ of interest for the treatment of human diseases (U.S. Pat. App. No. 2007/0116691). These immortalized stem cells can be used as a long term source for transplantation.

In a very recent article by Toyoshima et al (Nat. Commun. 2012, 3, 784), the authors demonstrated fully functional hair regeneration in a nude mouse model using bioengineered hair follicle germ transplanted intracutaneously. The bioengineered hair follicle germ was a bioengineered vibrissa follicle germ reconstituted with adult follicle-derived cells. This approach is very promising but transplantation requires invasive surgery to introduce the bioengineered hair follicles. It was not yet determined if these engineered follicles remain capable of producing hair in the long term. All of these studies will need to reproduced in humans to completely understand if stem cell transplantation will work in human subjects.

A new alternative topical treatment for hair loss was reported using an FDA-approved glaucoma drug, bimatoprost, that is commercially available to lengthen eyelashes may also be able to induce the growth of hair in the human scalp. Clinical trials are underway to determine if the bimatoprost is effective beyond growing and thickening hair in androgenetic alopecia where the hair follicle is deficient in progenitor matrix cells.

In a Canadian Application, CA2008/002019, related to the present invention, applicants reported that GCSF subcutaneously injected into mice at a similar dose as that used in humans, where the mice were shaved and treated with depilatory cream, showed an approximate 20% increase in hair growth as well as it was noted the hair had thicker shafts. Other factors in conjunction with GCSF promoting hair growth and hair thickening in mice included Vascular Endothelial Growth Factor and Epidermal Growth Factor. In same invention, the applicants used a model of temporary hair loss to study the effect of GCSF or other factors. Mice were injected with cyclophosphamide, a chemotherapy drug, to inhibit hair growth. It should be noted that a side effect of GCSF treatment in chemotherapy patients for neutropenia is hair loss. Surprisingly, the applicants used over 10 fold higher dose rate per kilogram than used in human therapies and their previous study in patent application. In both untreated and treated mice, hair grew however the rate of hair growth in mice injected with the large dose of GCSF showed a two fold increase in hair growth compared to control. It should be noted that GCSF was given one day after injection with cyclophosphamide, suggesting that the effect would be protective. The hair growth in control mice underscores that the model does not to accurately reflect the deficient stem cells in androgenetic alopecia.

In the present invention, it was surprisingly found that GCSF was able to re-grow hair when administered in multiple consecutive courses of GCSF. Further, the hair that was restored was retained upon less frequent, routine administration of GCSF administered. In addition, GCSF was able to increase both fingernail cuticle growth and density.

EXAMPLE 1

Reversal of Symptoms with Parkinson's Disease with Granulocyte-Colony Stimulating Factor The patient was a 61 year-old male with a six year history of Parkinson's Disease. When first diagnosed two years prior, the patient was started on 100 milligrams Amantidine twice daily and 5 milligrams Selegiline twice daily and on increasing doses of Permax, 25 micrograms to 250 micrograms three times daily.

A history taken immediately before starting the dosing of Granulocyte-Colony Stimulating Factor (GCSF) was typical of adult onset Parkinson's disease. The patient had blood work performed 7 days before treatment which included CBC, ESR, urine analysis and chemistry screen. In summary, the male patient, approximately 67 kg body weight diagnosed with Parkinson's Disease had history of modest hyperlipidemia which was controlled on medications. Physical exam was normal except for some cogwheeling especially on the right. Granulocyte-Colony Stimulating Factor was started at a daily dose of 330 micrograms (1.1 ml) through injection for 5 consecutive days. Patient experienced slight bone pain on second and third days of therapy. About 3 weeks after Granulocyte-Colony Stimulating Factor therapy was started, patient realized that he could smell, something that he had not been able to do for more than 5 years. This observation is consistent with improvement in olfactory nerve function. About a week later, the patient found that the orthostatic hypotension that had given him trouble for the last 2-3 years and had required him to wear support stockings, had disappeared. In addition, the patient was able to stand up quickly from a sitting position or walk up stairs without becoming severely light-headed. The patient's handwriting, previously totally unreadable, was greatly improved and was legible to others. It was observed by his wife that the patient had an improved facial affect. After about two months, a plateau was reached.

Surprisingly, it was found that Granulocyte-Colony Stimulating Factor treatment of a patient with Parkinson's disease was followed four weeks later by quantifiable evidence of efficacy utilizing symptoms that indicated an effect on both the Central Nervous System and Peripheral Nervous System (PNS). The patient improved in several CNS symptoms that included resting tremor, rigidity, postural instability, and micrographia. Four accepted PNS symptoms of Parkinson's disease, the loss of sense of smell, orthostatic hypotension and urinary and gastrointestinal incontinence disappeared during the third and fourth weeks following the start of therapy. The disappearance of orthostatic hypotension was not complete but was greatly reduced. Unexpectedly, GCSF caused reversal of one or more symptoms of Parkinson's Disease upon treatment with the first dose. The reversed symptoms included orthostatic hypotension, resting tremor, rigidity, postural instability, handwriting and urinary and gastrointestinal incontinence.

EXAMPLE 2

Long Term Treatment of Parkinson's Disease Using Granulocyte-Colony Stimulating Factor The long term treatment of Parkinson's Disease by GCSF was followed using a standardized system approved by neurologists, the Unified Parkinson's Disease Scale (UPDS), to more completely access the efficacy of treatment. UPDS utilizes over 40 distinct clinical evaluations that are predominantly based mostly on CNS symptoms. Analysis was performed approximately 2 to 4 weeks after injection of the first dose. To more fully understand the effect of the GCSF, the data was analyzed to determine whether a correlation existed between dose of GCSF and reversal of symptom score. The patient received injection of the same dose of GCSF every six to eight weeks and was periodically evaluated by UPDS criteria. In FIG. 1, the score of UPDS was plotted over the course of two and one-half years. The correlation coefficient was −0.93 suggesting the reversal was progressive upon GCSF treatment and was statistically significant (P=0.001). The final score obtained by the patient approached the score that a non-patient might receive.

Because UPDS evaluates mostly CNS symptoms of Parkinson's Disease, four indicators of PNS symptoms were also evaluated included urinary and gastrointestinal incontinence, orthostatic hypotension and loss of smell. The induction of orthostatic hypotension was evaluated by taking blood pressure before and after going from a lying down position to sitting and then standing position and each time taking blood pressure with an automatic apparatus. A drop of 50 mm was associated with developing lightheadedness and orthostatic hypotension. All four indicators were reversed relative to the state prior to GCSF treatment. In fact, the patient was able to exercise without fainting or having to rest (orthostatic hypotension), enjoyed foods and wine (smell), resolved urinary and gastrointestinal incontinence, and gained sense of smell resulting in a higher quality of life.

EXAMPLE 3

Reduction of Blood Glucose Levels in Type 2 Diabetics Administered with Granulocyte-Colony Stimulating Factor Other benefits were observed upon treatment with Granulocyte-Colony Stimulating Factor in the same patient as described in Example 1. The patient exhibited a two year history of slightly elevated blood glucose determinations (average fasting blood sugar ranging up to 115 mg/Dl). Patient had a slightly elevated hemoglobin A1C (6.5 versus normal of <6.0. He was diagnosed as Type 2 Diabetes and was recommended to a Diabetics clinic for classes on diet and exercise for dealing with this disease. Although dieting and exercise provided some reducing it was not solely sufficient in controlling blood glucose levels below the 110 mg/dl.

After treatment with Granulocyte-Colony Stimulating Factor it was observed that the blood sugar averaged 104 mg/Dl for 15 specimens before treatment and decreased to 92 mg/Dl during the period starting three weeks after the start of drug (and at the same time that Parkinson's symptoms disappeared. The difference was highly significant (P=0.001).

EXAMPLE 4

Figure 3:
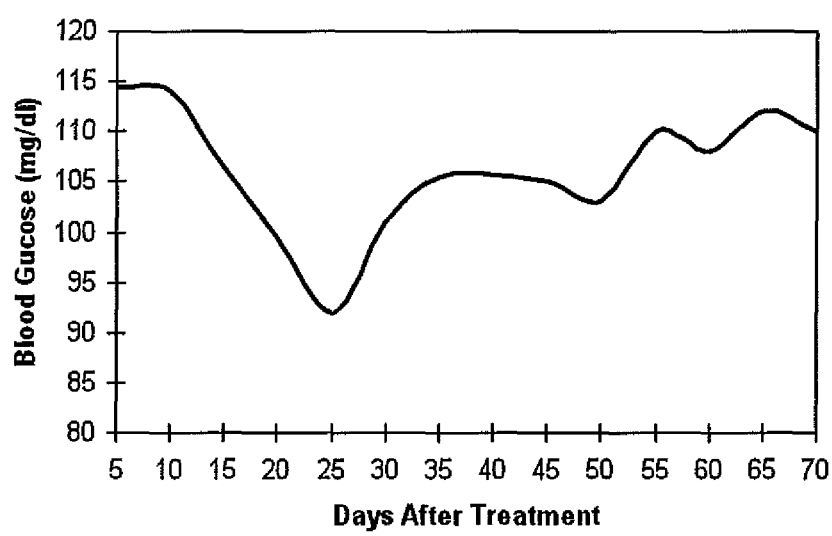
FIG. 3 shows the average time course for blood glucose levels of six treatments with GCSF.
Figure 4:
FIG. 4 shows a GCSF treated identical twin and untreated identical twin with different hair losses.
Figure 4:
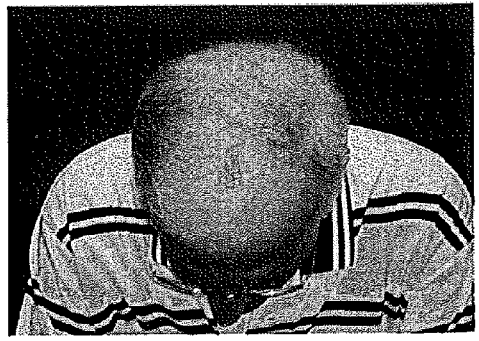
Figure 4:
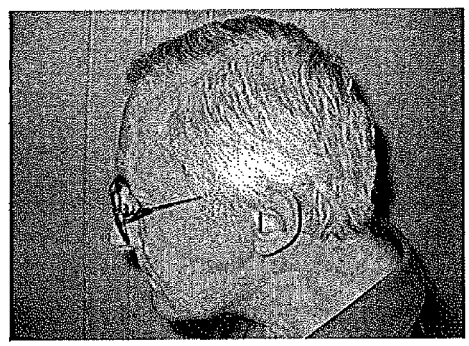
Figure 4:
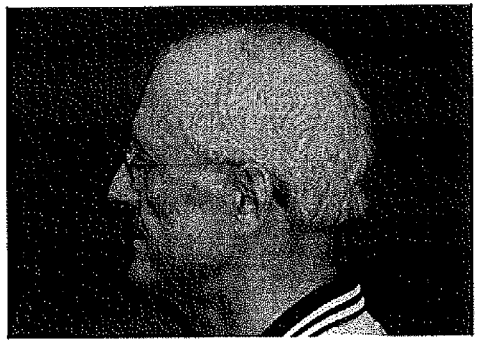

Long Term Controlled Reduction of Blood Glucose Levels in Type 2 Diabetics Administered with Granulocyte-Colony Stimulating Factor To examine the long term effect of Granulocyte-Colony Stimulating Factor on a patient with adult onset Type 2 diabetes, the patient in Example 2 was monitored for approximately two and one-half years for fasting blood glucose almost every morning. Starting with the first day of therapy with GCSF, every 5 day period was averaged and the mean used to compare blood glucose levels. FIG. 3 shows the analyzed data from blood sugar determinations around six courses of GCSF. Each time after the GCSF is administered the blood sugar dropped well within the normal range after about twenty to thirty days after the start of therapy. In one case drug was not administered until late in the period of follow-up and then the nadir was reached about twenty-five days after the start of that course. All curves reached a nadir ranging between 20 and 30 days after the start of therapy. Most blood glucose determinations remained below 110 mg/Dl for about 2 months after treatment. It was unexpected that a drug, and more surprising GCSF, is able to reduce blood glucose for extended periods beyond one day, even more surprising one week and most surprising one month. The patient was also able to ingest limited amounts of Dove® bars without any problems. GCSF provides a consistent and more desirable approach to regulate blood glucose levels in Type 2 diabetics with less potential side effects of multiple mechanisms employed to control Type 2 diabetes beyond other drugs.

EXAMPLE 5

GCSF Supplemental Production of Stem Cells in a Close Donor or Self to Improve Control in the Reduction of Blood Glucose Levels in Type 2 Diabetics An individual was treated with stem cells obtained from self or a close relative as a way to increase the effect of GCSF in controlling on blood glucose levels. In the later case, an identical twin was examined for MHC profile and found to be a match. To produce a supplemental amount of stem cells in the identical twin, the twin was administered Granulocyte-Colony Stimulating Factor a daily dose of 330 micrograms through injection for 5 consecutive days. Patient experienced slight bone pain on second and third days of therapy. After 7-10 days, the blood of the patient was subjected to leukaperesis to collect peripheral blood stem cells from the mobilized peripheral blood progenitors. Preferably, CD34+ stem cells are isolated from peripheral blood stem cells and HLA matched donors.

The stem cells obtained from a Neupogen-treated twin were injected into the patient with Type 2 diabetes that was previously treated with GCSF. After 1-2 weeks, the patient was administered a course of GCSF; 330 micrograms (1.1 ml) through injection for 5 consecutive days. It was found that the level of blood glucose decreased significantly from the prior treatment and remained lower for a longer period that the prior treatment.

The exogenous treatment using isolated stem cells of the Type 2 diabetic patient was also repeated with the patient's own stem cells, however the increase was less than that observed with treatment of stein obtained from the identical twin. Preferably, self-produced stem are harvest from the individual when the individual is a young adult between the ages of 16 to 35 years of age. The optimal ages are between 18 and 30 years of age. The harvested stem cells are subjected to preservation methods, such as cryopreservation until needed.

EXAMPLE 6

GCSF Acceleration of Hair Growth and Fingernail Growth and Density

Yet other benefits of the Granulocyte-Colony Stimulating Factor treatment observed was the re-growth of hair in a human patient with androgenic alopecia.

To re-grow of hair in the balding scalp, the patient was treated with an increased frequency of the courses of Neupogen administered. Prior to treatment, the patient had received courses of GCSF as described in Example 2 and Example 4, however no significant re-growth of hair was observed. Prior to the increased frequency of treatment, the patient exhibited moderate hair loss and thinning, corresponding to a rating of 5 on Hamilton-Norwood Scale for hair loss, ranging from 0 for no hair loss to 7 being complete hair scale loss. Neupogen (480 ug; 5-6 ug/kg body weight) was administered for each day for four days followed by a period of no treatment for four days. This regimen was repeated for a total of six times consecutively. After the patient continued on their normal periodic treatment of GCSF, being administered with GCSF courses every 6-18 weeks. Surprisingly, about 4-6 months after GCSF treatment, the substantial growth of new hair, or re-growth of hair, on the subject's scalp resulted in a improvement of hair growth to 2 on the Hamilton-Norwood Scale. The hair was similar in texture and distribution to early stages of male pattern baldness in the individual. In dramatic comparison to the patient's identical twin, as shown in FIG. 5, the untreated twin brother had a rating of 6 on the Hamilton-Norwood Scale. Both individuals had a similar amount of hair loss prior to administration of GCSF to the treated patient.

After the increased courses were completed, the administration of Neuprogen returned to a treatment of every 6-18 weeks. It was observed the hair grew much more quickly in the months following administration of the increased courses. The rate of hair growth and density has been maintained the same growth since the patient treatment has returned to routine courses during the past 2 years. These findings showed that once the amount of desired hair growth is obtained, the lower frequency rate is suitable to retain hair growth.

For consecutive courses, GCSF is administered for about 3 to 6 days and the treatment is repeated about every 3 to 8 days for two or more consecutive courses, preferably 3 to 6 courses. The administration of effective consecutive courses and periodic courses of GCSF is administered at a daily dose rate of 0.1 ug to 100 ug, preferably 0.1 to 10 ug per kg, more preferably 0.1 to 5 ug per kg and most preferably 0.1 to 2 ug per kg body weight.

Other factors can be used to supplement hair growth and density with GCSF administration. For example, based on bimaprost findings stimulating hair growth and thickening, bimaprost, and like compounds working on related receptors in the follicle area, may be effective to increase hair volume once the damaged progenitor stem cells have been replenished. Other factors that may enhance include Vascular Endothelial Growth Factor and Epidermal Growth Factor reported earlier to stimulate hair growth. GCSF treatment would also be effective as a companion treatment for stem cell transplantation either prior to, after or both, including preconditioning of the stem cells with GCSF prior to transplantation.

This is the first report where GCSF was demonstrated to re-store hair growth in a human patient with androgenic alopecia. The results showed that GCSF was able to restore hair matrix cells functionality to growth hair and further treatments could obtain additional hair growth. The consecutive course regimen of GCSF not only mobilizes progenitor stem cells but also facilitates their maturation into hair producing matrix cells. It is surprising that many references have suggested that hair loss may occur with GCSF treatment, however this may be complicated by the fact that GCSF in limited courses in chemotherapy.

Because the hair matrix cells are similar to fingernail matrix cells, it was also observed that the cuticle density and growth improved dramatically during the same period. Prior to treatment, the fingernails of patient were very flexible and had a slow growth rate as well as the nails were often chipped. In the same subject treated with the multiple courses of GCSF administration described for hair re-growth, it was found that the fingernails had become much denser and grew at a faster rate similar to that observed for their hair. Identical effective consecutive courses and periodic courses of GCSF for hair would used be for cuticle, fingernail and toe nail GCSF treatments.

Other Embodiments

The description of the specific embodiments of the invention is presented for the purposes of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications, and publications referenced herein are hereby incorporated by reference. Other embodiments are within the claims.

The invention claimed is:

1. A method for the re-growth of hair in a patient with male or female pattern baldness alopecia by administering effective courses of Granulocyte-Colony Stimulating Factor or its functionality improving modifications, comprising;
   a. administering the effective course of Granulocyte-Colony Stimulating Factor to the patient, wherein the effective course is administering an effective dose of Granulocyte-Colony Stimulating Factors for 3 to 6 days;
   b. providing no treatment of Granulocyte-Colony Stimulating Factor to the patient for 3 to 8 days;
   c. steps a and b are repeated 1 to 5 times; and
   d. upon completion of step c, administering the effective course of Granulocyte-Colony Stimulating Factor to the patient every 2 to 18 weeks for 4 to 6 months.

2. The method of claim 1, wherein the effective dose is 0.1 micrograms to 10 micrograms per kg body weight per day of Granulocyte-Colony Stimulating Factors.

3. The method of claim 1, wherein administration is performed either by said administered is selected from a group consisting of subcutaneous injection, or intravenously.

4. The method of claim 1 to maintain hair growth by administering periodic effective courses of Granulocyte-Colony Stimulating Factor or its functionality improving modifications, wherein the periodic courses maintain the hair growth, further comprising;
   a. administering the periodic effective course, wherein the periodic course is an effective dose of Granulocyte-Colony Stimulating Factors administered for 3 to 6 days; and
   b. repeating the administration of the periodic effective course every 2 to 18 weeks to maintain hair growth.

5. The method of claim 4, wherein the effective dose of Granulocyte-Colony Stimulating Factor is 0.1 micrograms to 10 micrograms per kg body weight per day of Granulocyte-Colony Stimulating Factor on each day.

6. The method of claim 5, wherein administration is performed either by said administered is selected from a group consisting of subcutaneous injection, or intravenously.

7. A method to maintain hair growth by administering periodic effective courses of Granulocyte-Colony Stimulating Factor or its functionality improving modifications to a patient with male or female pattern baldness alopecia, wherein the periodic courses maintain the hair growth, comprising;
   a. administering the periodic effective course, wherein the periodic effective course is an effective dose of Granulocyte-Colony Stimulating Factors administered for 3 to 6 days; and
   b. repeating the administration of the periodic effective course every 2 to 18 weeks to maintain hair growth.

8. The method of claim 7, wherein the effective dose of Granulocyte-Colony Stimulating Factor is 0.1 micrograms to 10 micrograms per kg body weight per day of Granulocyte-Colony Stimulating Factor on each day.

9. The method of claim 5, wherein administration is performed either by said administered is selected from a group consisting of subcutaneous injection or intravenously.

* * * * *